United States Patent [19]

Tromovitch

[11] 4,043,341
[45] Aug. 23, 1977

[54] PORTABLE CRYOSURGICAL INSTRUMENT

[76] Inventor: Theodore A. Tromovitch, 1667 Escalante Way, Burlingame, Calif. 94010

[21] Appl. No.: 639,081

[22] Filed: Dec. 9, 1975

[51] Int. Cl.² .................. A61B 17/36; B65D 47/34
[52] U.S. Cl. ............................. 128/303.1; 222/209; 222/470
[58] Field of Search ............ 128/303.1; 401/185; 222/209, 470

[56] References Cited
U.S. PATENT DOCUMENTS

| 879,951 | 2/1908 | Elias | 222/209 |
|---|---|---|---|
| 947,468 | 1/1910 | Fish | 222/209 |
| 1,485,126 | 2/1924 | Schumacher | 401/185 X |
| 3,537,458 | 11/1970 | Lange et al. | 128/303.1 |
| 3,613,689 | 10/1971 | Crump et al. | 128/303.1 |
| 3,651,813 | 3/1972 | Bryne | 128/303.1 |
| 3,702,114 | 11/1972 | Zacarian | 128/303.1 |
| 3,823,718 | 7/1974 | Tromovitch | 128/303.1 |
| 3,889,681 | 6/1975 | Waller et al. | 128/303.1 |
| D. 30,935 | 6/1899 | Ryan | D23/1 |

Primary Examiner—Channing L. Pace
Attorney, Agent, or Firm—Robert Charles Hill

[57] ABSTRACT

A portable cryosurgical instrument suitable for one handed operation is provided with means to precisely control the amount of spray discharge necessary in order to necrotize the desired tissue.

2 Claims, 2 Drawing Figures

PORTABLE CRYOSURGICAL INSTRUMENT

BACKGROUND OF THE INVENTION

The use of an cryosurgical apparatus to freeze healthy or diseased tissue in order to necrotize the same is gaining widespread acceptance in the medical profession, particularly among dermatologists. As a result, a number of cryosurgical instrument have been developed and offered in the marketplace in the last few years.

Careful analysis of the problems encountered with the existing prior art devices led to the conclusion that the ideal cryosurgical instrument should provide optimum use of the liquefied gas coolant, produce a predominately spray rather than liquid discharge, have an extremely delicate and precise control of the amount of coolant delivered, and be easily capable of one handed operation by the operator. Unfortunately, as will be seen below, none of the devices on the market possess all of these desired attributes.

A cryosurgical apparatus in common use today by the medical profession is shown in U.S. Pat. No. 3,823,718 issued to the instant inventor. While this apparatus has an insulated container to conserve the liquefied gas coolant and tubing of a sufficient length to produce a predominately spray discharge, it requires two hands to operate and does not have precise control of the amount of coolant delivered.

Another apparatus that is being sold in the market today is shown in U.S. Pat. No. 3,889,681 issued to Waller et al. Since the liquid coolant is contained in a vacuum bottle, considerable waste of the liquid coolant is avoided. Precise control of the amount of coolant is also provided. However, two hands are required for operation (see column 3, lines 36–42). Additionally, attaching a needle directly to the outlet nozzle does not allow the pressurized liquefied gas coolant to vaporize to a sufficient degree with the result that an excess amount of liquid drips off of the needle, thereby causing unnecessary danger during the cryosurgery.

Other instruments used at the present time include those shown in the Brynes patents, U.S. Pat. No. 3,534,739 and 3,651,813, and the patent issued to Reynolds, U.S. Pat. No. 3,739,956. The drawbacks of these devices have been adequately described in U.S. Pat. No. 3,889,681.

The present invention eliminates all the problems inherent in the above described devices. The present invention conserves the liquefied gas coolant by utilizing an insulated container, produces a predominately spray discharge by providing heat exchange means intermediate the application means and the tubing means, affords precise control of the amount of coolant delivered by means of an aperture on the manual squeeze bulb, and is easily capable of one handed operation by the operator because of the adjacent relationship of the handle means and the source of pressurized air.

SUMMARY OF THE INVENTION

It is the primary object of the present invention to provide a new and improved portable cryosurgical instrument.

Another object of the invention is to provide an instrument that minimizes waste of the liquid coolant and produces a predominately spray discharge.

A further object of the invention is to provide an instrument which is easily capable of one handed operation by the operator while at the same time providing precise control of the amount of coolant delivered.

A still further object is to provide structure which is inexpensive to manufacture and long lasting in usage.

DESCRIPTION OF THE PREFERRED EMBODIMENT

Figures 1, 2:
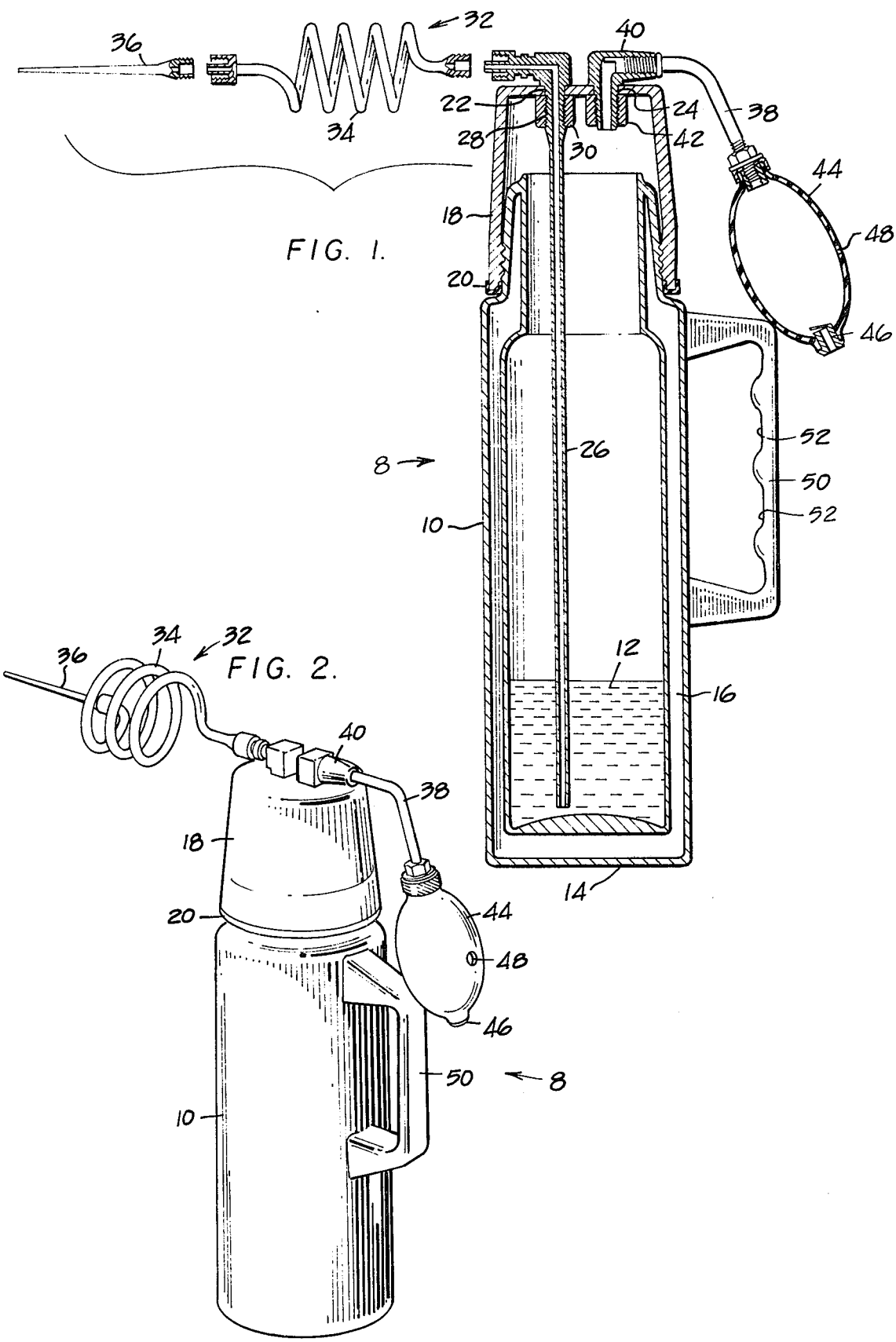
FIG. 1 is a side elevation cross-sectional view of the portable cryosurgical instrument of the present invention.
FIG. 2 is a perspective view of the instrument in operation on a patient.

Referring now to FIG. 1, there is illustrated a portable cryosurgical instrument, generally indicated 8, including a supply container 10 having a suitable cryogenic liquid 12 contained therein. The container 10 comprises a base member 14 into which is seated an insulated bottle 16 which is preferably a double walled vacuum bottle. The upper portion of the insulated container 10 consists of a cap 18 threadably connected thereto with a sealing ring 20 providing a good seal therebetween.

Holes 22 and 24 are contained within cap 18. Tubing 26 extends from near the bottom of the container through hole 22 to the atmosphere. Tubing 26 is of a suitable noncorrosive metal substance for receiving the liquefied gas coolant 12 contained inside container 10. Thread connections 28 of tubing 26 cooperates with retaining nut 30 to securely locate the tubing 26 to the cap 18.

Attached to tubing 26 is heat exchange means 32 for vaporizing the liquefied gas coolant passing therethrough. The heat exchange means can be a plurality of coils 34 or some other configuration which allows the ambient temperature to vaporize the liquid. It has been found that a series of 4 or 5 small coils produce about 90% vapor and 10% liquid, a very desirable ratio. Attached to the heat exchange means 32 is nozzle or application means 36 for applying the vaporized gas coolant to the patient. Both the heat exchange means 32 and the nozzle 36 can be attached by the familiar Leur type locking arrangement well-known in the art.

Pressure line 38 is threadably received into flange fitting 40 and communicates with the inside of container 10 through hole 24. Nut 42 holds flange 40 in place. A source of pressurized air in the form of a manual squeeze bulb 44 is connected to the pressure line 38. The bottom of the squeeze bulb 44 has a one-way Reed valve 46 that allows air to flow into the bulb 44 but not vice versa. Opening 48 connects the bulb 44 to the atmosphere. In this manner the opening 48 is adapted for covering by the thumb of the operator of the squeeze bulb 44 to stop venting before pressurization and to instantaneously remove pressurization upon uncovering.

Pressure line 38 is rigid metal tubing of sufficient length so that the squeeze bulb 44 attached thereto is adjacent handle 50 having gripping portions 52. Thus it can be seen that the handle 50 is adapted for gripping by the fingers of the operator and the opening 48 is adapted for covering by the thumb of the operator to stop venting before pressurization whereby the thumb compresses the bulb 44 against the handle 50 to cause pressurization. This above described one handed operation can be very important. With one hand free, the operator is able to touch the patient before and during application to impart a desired relaxing effect thereto. In other instances the other hand of the operator can be used to hold a colimating device such as a funnel or cylinder to the skin of the patient and thereby limit the area of freeze produced by the coolant.

During operation of the instrument of the present invention, the container 10 is filled with liquefied gas coolant 12, such as liquid nitrogen, to a suitable level. Vent provided through aperture 48, squeeze bulb 44, pressure line 38 and flange fitting 40 prevent any excessive pressures from building up within the container 10. The operator grips the handle 50 with fingers and places the thumb over opening 48 while simultaneously compressing the bulb 44 against handle 50. The compression of the squeeze bulb 44 creates a pressure inside container 10 thereby forcing the liquid nitrogen up tubing 26 through coils 34 where it is vaporized and out nozzle 36 in a predominately spray discharge onto the tissue to be necrotized. As soon as the desired amount of coolant has been applied, the thumb can be removed from opening 48. This will immediately relieve the pressure inside the container 10 thereby stopping the flow of spray out nozzle 36.

It can thus be seen that the present invention conserves the liquefied gas coolant by utilizing an insulated container, produces a predominately spray discharge by providing heat exchange means intermediate the application means and the tubing means, affords precise control of the amount of coolant delivered by means of an aperture on the manual squeeze bulb, and is easily capable of one handed operation by the operator because of the adjacent relationship of the handle means and the source of pressurized air.

What is claimed is:
1. A portable cryosurgical instrument suitable for one handed operation comprising:
   an insulated container for holding a liquefied gas coolant;
   closure means for said insulated container;
   a pressure line communicating with the inside of said insulated container;
   tubing means extending from near the bottom of said insulated container to the outside thereof;
   heat exchange means attached to said tubing means outside said container for vaporizing said liquefied gas coolant passing therethrough;
   application means attached to said heat exchange means for applying the vaporized gas coolant;
   handle means on said insulated container;
   a manual squeeze bulb connected to said pressure line and positioned adjacent said handle means in such position that when the fingers of a human hand grasp the handle, the thumb of the same hand is in a position to compress the bulb against the handle;
   said squeeze bulb being connected to atmosphere through an opening in an intermediate portion of the bulb such that said opening must be covered before pressurization, wherein when said handle is gripped by the fingers of one hand of the operator, the bulb opening can be covered by the thumb of the same hand of the operator to stop venting before pressurization whereby the thumb compresses said bulb against said handle to cause pressurization.
2. The portable cryosurgical instrument of claim 1 wherein the manual squeeze bulb is positioned superjacent the handle means.

* * * * *